(12) United States Patent
Wang et al.

(10) Patent No.: US 12,083,014 B2
(45) Date of Patent: Sep. 10, 2024

(54) FIXING DEVICE FOR CLAMPING TISSUE

(71) Applicants: Sierra Valve LLC, Wilmington, DE (US); PEIJIA MEDICAL (SUZHOU) CO., LTD., Jiangsu (CN)

(72) Inventors: Kai Wang, Jiangsu (CN); Jian Fong Tan, Jiangsu (CN); Yi Zhang, Jiangsu (CN)

(73) Assignees: Sierra Valve LLC, Wilmington, DE (US); PEIJIA MEDICAL (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 18/591,034

(22) Filed: Feb. 29, 2024

(65) Prior Publication Data

US 2024/0197477 A1 Jun. 20, 2024

Related U.S. Application Data

(63) Continuation of application No. 18/217,524, filed on Jun. 30, 2023, now Pat. No. 11,957,585, which is a continuation of application No. PCT/CN2021/105806, filed on Jul. 12, 2021.

(30) Foreign Application Priority Data

Dec. 30, 2020 (CN) .......................... 202011620974.1

(51) Int. Cl.
*A61F 2/24* (2006.01)

(52) U.S. Cl.
CPC .......... *A61F 2/2463* (2013.01); *A61F 2/2466* (2013.01); *A61F 2220/0008* (2013.01); *A61F 2220/0041* (2013.01)

(58) Field of Classification Search
CPC .................. A61F 2/2463; A61F 2/2466; A61F 2220/0008; A61F 2220/0041; A61F 2/24; A61F 2/246; A61F 2/2427
See application file for complete search history.

(56) References Cited

FOREIGN PATENT DOCUMENTS

CN 211560531 U * 9/2020

OTHER PUBLICATIONS

CN 211560531 U Translation (Year: 2019).*

* cited by examiner

*Primary Examiner* — Brian A Dukert
*Assistant Examiner* — Rebecca Lynee Zimmerman

(57) ABSTRACT

A fixing device for clamping a tissue comprises a support mechanism comprising a fixed connecting assembly and a drive assembly, and a clamp mechanism comprising closure members and capture portions, wherein each closure member comprises a closure connecting portion and a closure clamping portion in cooperation with one of the capture portions to clamp the tissue; wherein each closure connecting portion is provided with guide slots comprising a first slot portion and a second slot portion in communication therewith and has a relatively smaller radian, the fixed connecting assembly is provided with pins at least partially located in the guide slots, respectively, and the pins are slidable relative to the guide slots when the drive assembly moves relative to the fixed connecting assembly, so as to drive the closure clamping portions to move towards or away from each other. A system comprising the fixing device, and a method are provided.

16 Claims, 11 Drawing Sheets

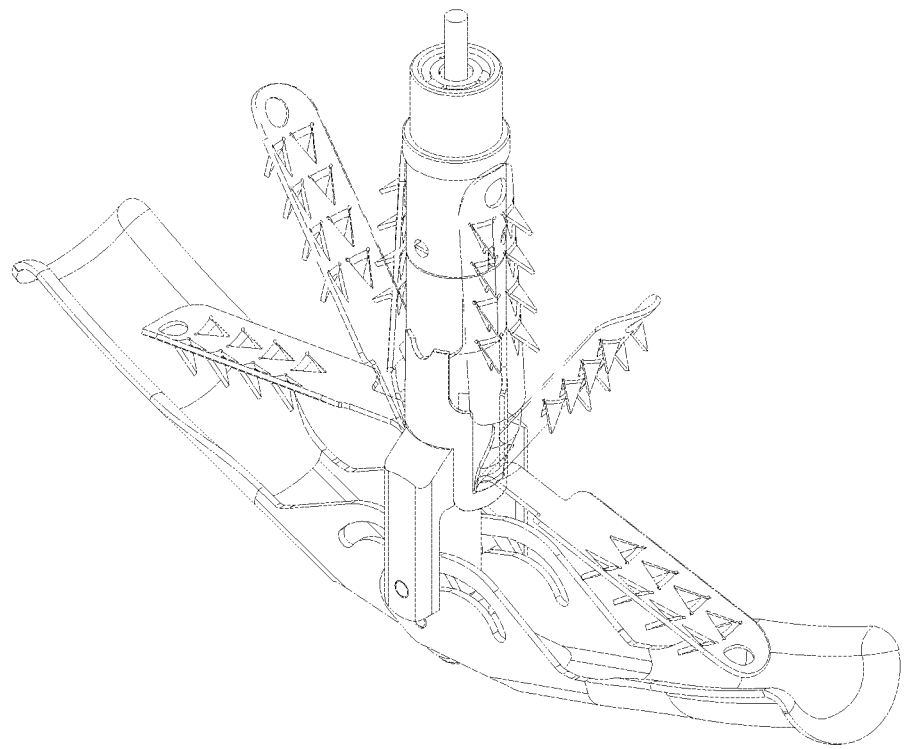
FIG.4
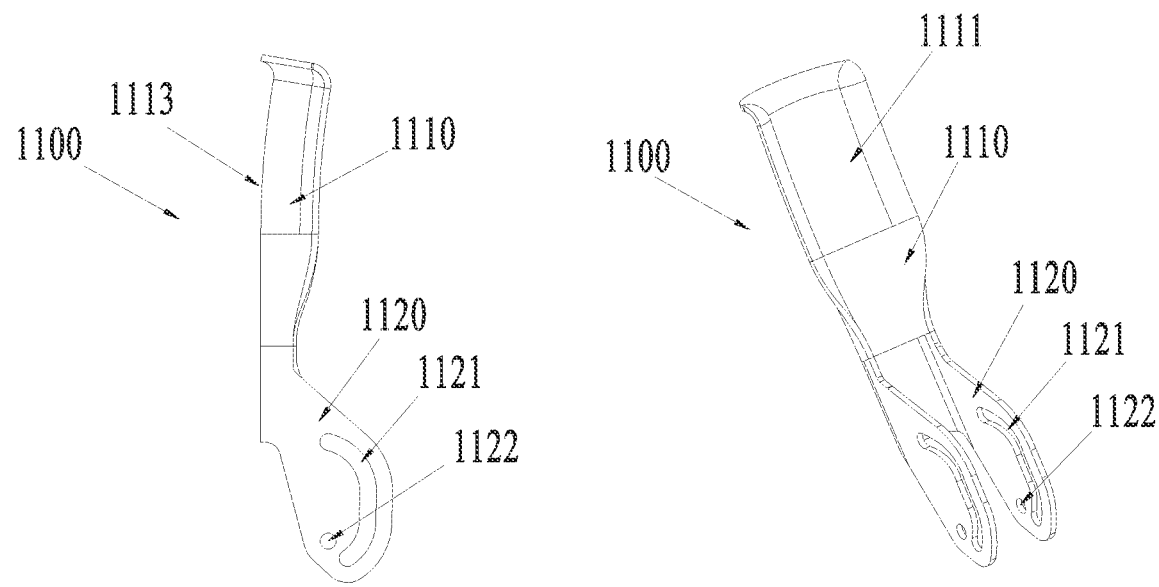
FIG.5A
FIG.5B

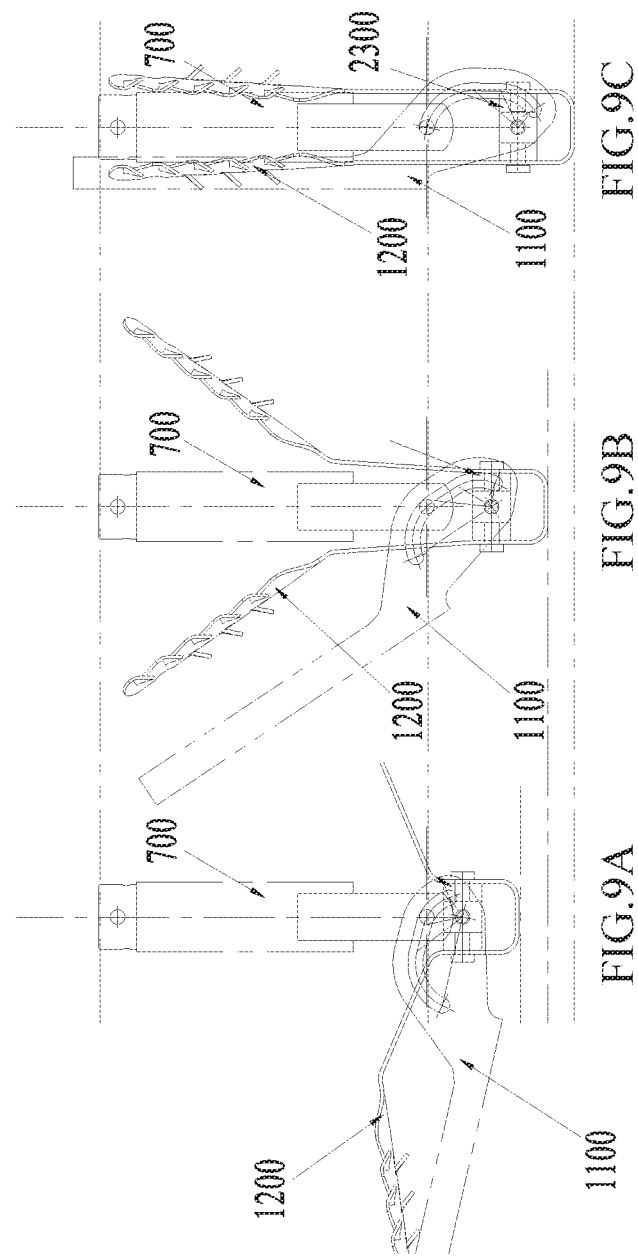

FIXING DEVICE FOR CLAMPING TISSUE

CROSS REFERENCE TO RELATED APPLICATIONS

The present application is a Continuation Application of U.S. application Ser. No. 18/217,524 filed on Jun. 30, 2023, which is a Continuation Application of PCT Application No. PCT/CN2021/105806 filed on Jul. 12, 2021, which claims the benefit of Chinese Patent Application No. 202011620974.1 filed on Dec. 30, 2020. All the above are hereby incorporated by reference in their entirety.

TECHNICAL FIELD

The present disclosure relates to a medical device, in particular to a fixing device for clamping tissue.

BACKGROUND

The mitral valve acts as a valve during the normal cycle of heart contraction to prevent oxygenated blood from flowing back into the left atrium, and the abnormal leakage of blood from the left ventricle to the left atrium is called mitral valve closure incomplete. Severe reflux can affect the pumping efficiency of the heart, putting patients at risk for severe, progressive heart failure.

The most common treatments for mitral valve regurgitation rely on prosthetic valve replacement, as well as valvuloplasty, such as rectangular posterior leaflet excision, chordae folds, edge-to-edge repair techniques, prosthetic chordae implantation techniques, Replacement and Repair These techniques typically rely on open-heart surgery, in which the patient's chest is opened, usually through a sternotomy, and the patient is placed on a cardiopulmonary bypass.

With the advancement of medical technology, conventional high-risk surgeries are being gradually replaced by minimally invasive catheter procedures. At present, minimally invasive techniques mainly developed and applied in markets include indirect annuloplasty, direct annuloplasty, edge-to-edge repair, and chordae tendineae repair, etc.

The edge-to-edge repair gradually becomes mature in clinical practices of surgical treatment for mitral valve regurgitation and has a desirable treatment effect. By suturing the valve edge of the prolapsed segment, the normal chordae tendineae on both sides of the diseased part are close to each other, so that the valve leaflets can be restored to the normal coaptation level, and the function of restoring the normal coaptation of the mitral valve is achieved. Its advantages are: 1. Directly treat the diseased part, and the treatment is accurate; 2. The valve margins are coapted, and the coaptation is firm; 3. The shaping is repeatable, which can ensure the best valve leaflet coaptation and the relationship with the remaining tissue; 4. Fully retain the leaflet tissue and reduce tension; 5. It can effectively prevent the posterior leaflet from moving forward due to excessive longitudinal folding of the tissue, causing complications.

Valve clamp devices developed based on the technical principle of the surgical edge-to-edge suture of the valve are currently most recognized due to high safety, simple technical principle, and high feasibility.

In the existing operation, the leaflet clamp is delivered to the mitral valve through the push device, and then the anterior and posterior leaflets of the mitral valve are simultaneously clamped by the opposite opening of the clamps, so that the anterior leaflet and the posterior leaflet of the mitral valve are separated. The leaflet is fixed to achieve the purpose of reducing mitral valve regurgitation; however, existing clamps are restricted in length to some extent, because they need to pass through narrow channels and make a turn, which limits a capturing distance. Moreover, existing connecting rod mechanisms for driving the clamp also limit a turning angle of the clamp, which makes it more difficult to capture a valve leaflet. To sum up, it is desired to improve both the driving means and the separating means of the clamp.

SUMMARY

In order to solve the above technical problems, the present disclosure provides a fixing device for clamping a tissue, such as a mitral valve, e.g., which may include an improved mechanism to the larger opening angle and the longer effective capturing distance of the closure members, so as to capture and clamp a valve leaflet more easily, stably and reliably.

Specifically, the present disclosure includes the following solutions:

A fixing device for clamping tissue, comprising:
  a support mechanism comprising a fixed connecting assembly and a drive assembly that moves relative to the fixed connecting assembly;
  a clamp mechanism comprising a pair of closure members and a pair of capture members, each capture member in one-to-one correspondence with a respective one of the closure members; the pair of closure members comprising closure connecting portions with the closure clamping portions in cooperation with the pair of capture members to clamp the tissue; the closure connecting portions are provided with guide slots each comprising at least a nonlinear segment;
  the pins provided on the fixed connecting assembly, and wherein the drive assembly is connected to the two closure clamping portions, and is arranged to allow each of the pins to slide in the respective one of guide slots when the drive assembly moves relative to the fixed connecting assembly, so as to drive closure clamping portions of the clamp mechanism to move towards or away from each other.

Further, the closure connecting portions are rotatably connected to the drive assembly at the distal end of the closure connecting portions.

Further, the closure connecting portions are rotatably connected to the drive assembly on the centripetal side of the guide slots on the closure connecting portion.

Further, each of the guide slots comprises at least first and second slot portions in communication with each other, and a radian of the first slot portion is greater than a radian of the second slot portion.

Further, each of the guide slots comprises a third slot portion in communication with the second slot portion and having a radian greater than the radian of the second slot portion, and wherein the second slot portion is located between the first slot portion and the third slot portion.

Further, the drive assembly comprises a drive connecting member, and side surfaces of the drive connecting member include first mounting surfaces and second mounting surfaces perpendicular to each other;
  the drive connecting member is hinged to the closure connecting portion through the closure member matching portion on the first mounting surfaces;
  each one of the capture members of the clamp mechanism includes a rigid capturing portion, a flexible connecting portion, and a capture connecting portion that are connected sequentially, the flexible connecting portion is located between the rigid capturing portion and the capture connecting portion, and the second mounting surfaces are fixedly connected to the capture connecting portion.

Further, the rigid capturing portion includes a rigid surface, and capturing barbules or barbs provided outside the rigid surface, the rigid surface is uniformly thick and is arranged in a bent shape.

Further, the closure clamping portions includes a free end and a connection end connected to the closure connecting portion, and an outer surface of the closure clamping portions at least partially shrinks inward from the connection end to the free end direction.

Further, the fixed connecting assembly may include a base housing with a base inner cavity formed therein, a base threaded portion may be provided in the base inner cavity, the drive assembly may include a drive shaft, the drive shaft may include a drive shaft threaded portion cooperating with the base threaded portion, and wherein a lead angle at which the base threaded portion is cooperating with the drive shaft threaded portion may be less than a friction angle.

Further, the base housing is further provided with a base lug at the distal end. The pin is disposed outside the base lug.

A system for clamping a tissue, comprising
a fixing device comprising a clamp mechanism for closing a tissue, and a support mechanism carrying the clamp mechanism;
a delivery control device comprising a shaft for introducing the fixing device to a target location and a grasping mechanism for enabling the shaft and the fixing device to be separably connected.

Further, the clamp mechanism comprises a pair of closure members, a guide slot comprising at least a nonlinear segment in each of the pair of closure members, the support mechanism comprising pins, each of which is at least partially located in one of the guide slots and is slidable in the one of the guide slots, so as to drive closure clamping portions of the clamp mechanism to move towards or away from each other.

A method for repairing a tissue, comprising: delivering a fixing device to a target location; adjusting the closure members of the fixing device to approach/contact the tissue; controlling the capture members of the fixing device to clamp the tissue between closure members and capture members; adjusting the closure members to a right position before the fixed component self-locks.

The present disclosure achieves the following beneficial effects.
1) By improving driving methods and employing the guide slot(s) having nonlinear segment(s) for cooperative driving, and changing an opening angle and a capturing distance of the closure member, the present disclosure makes it easy to capture a valve leaflet, achieves more contact with the valve leaflet, and/or makes the valve leaflet to be captured more firmly.
2) By sequentially providing the first guide slot region, the second guide slot region and the third guide slot region, the closure member may have a relatively smaller torque and a faster change process during opening at an initial position and at a position with a maximum opening angle compared with the intermediate capturing process, and meanwhile may have a relative slow angular change at the capturing process, thereby facilitating fine operation by the operator, and improving system reliability.
3) The closing clamping part has the effect of pulling to the distal end, so that the closing process has a "biting" motion characteristic. On the premise that the tissue is firmly clamped, the valve leaflet on the closing clamping part will have a "pulling" effect., so that the leaflet and the closed clamping part are in firmer contact.
4) Adding some enlarge frictional force features or spur features on the rigid part of the catch, such as the catch spur in this embodiment, will make the effect of "pulling" the leaflet more obvious, compared to the background technology that only flips the moving proximal element, the present invention will make the combination of the leaflet and the fixation device more secure.

BRIEF DESCRIPTION OF THE DRAWINGS

In order to illustrate the technical solutions in the embodiments of the present disclosure more clearly, the drawings for the description of the embodiments or the prior art are briefly described below. Apparently, the accompanying drawings described below are merely some embodiments of the present disclosure, and those of ordinary skill in the art may still derive other drawings from these accompanying drawings without creative efforts.

FIG. 4 is a principle schematic view illustrating a capture member in indifferent states, according to one example of the present disclosure;

FIG. 5A is a side view of an exemplary closure member according to the present disclosure;

FIG. 5B is a schematic structural view of an exemplary closure member according to the present disclosure;

FIGS. 9A-9C each illustrate a movement of an exemplary closure member and capture member in a clamping process according to the present disclosure;

DETAILED DESCRIPTION

The technical solutions of the embodiments of the present disclosure are clearly and completely described below with reference to the accompanying drawings. Apparently, the described embodiments are merely a part rather than all of the embodiments of the present disclosure. In the description of the embodiment, the term "proximal end" refers to an end proximal to the operator, while the term "distal end" refers to an end distal to the operator. All other embodiments obtained by those of ordinary skill in the art based on the embodiments of the present disclosure without making inventive efforts shall fall within the scope of protection of the present disclosure.

Embodiment 1

Figure 2:
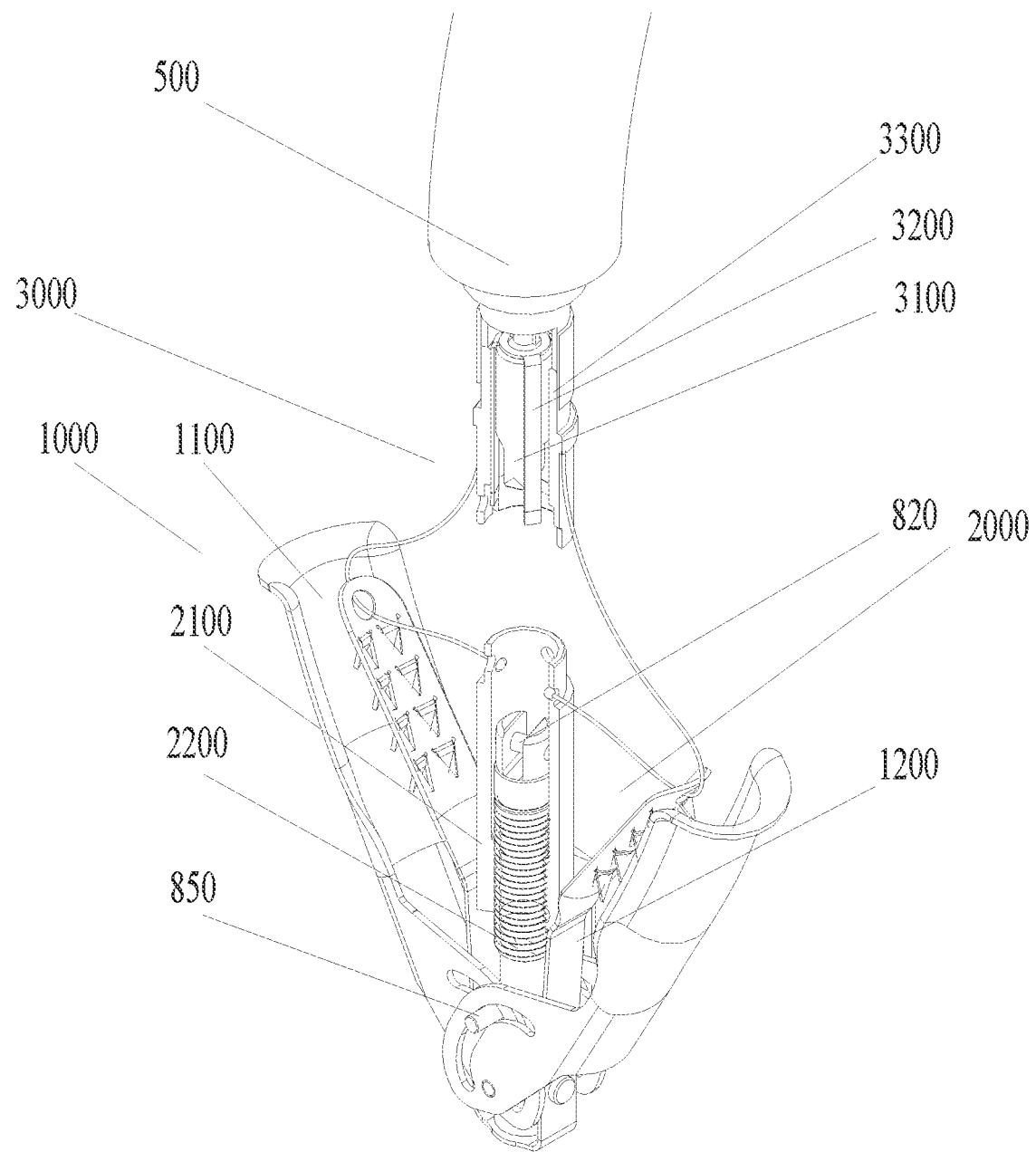
FIG. 2 is a schematic view of an example of an overall structure according to the present disclosure.
Figure 3:
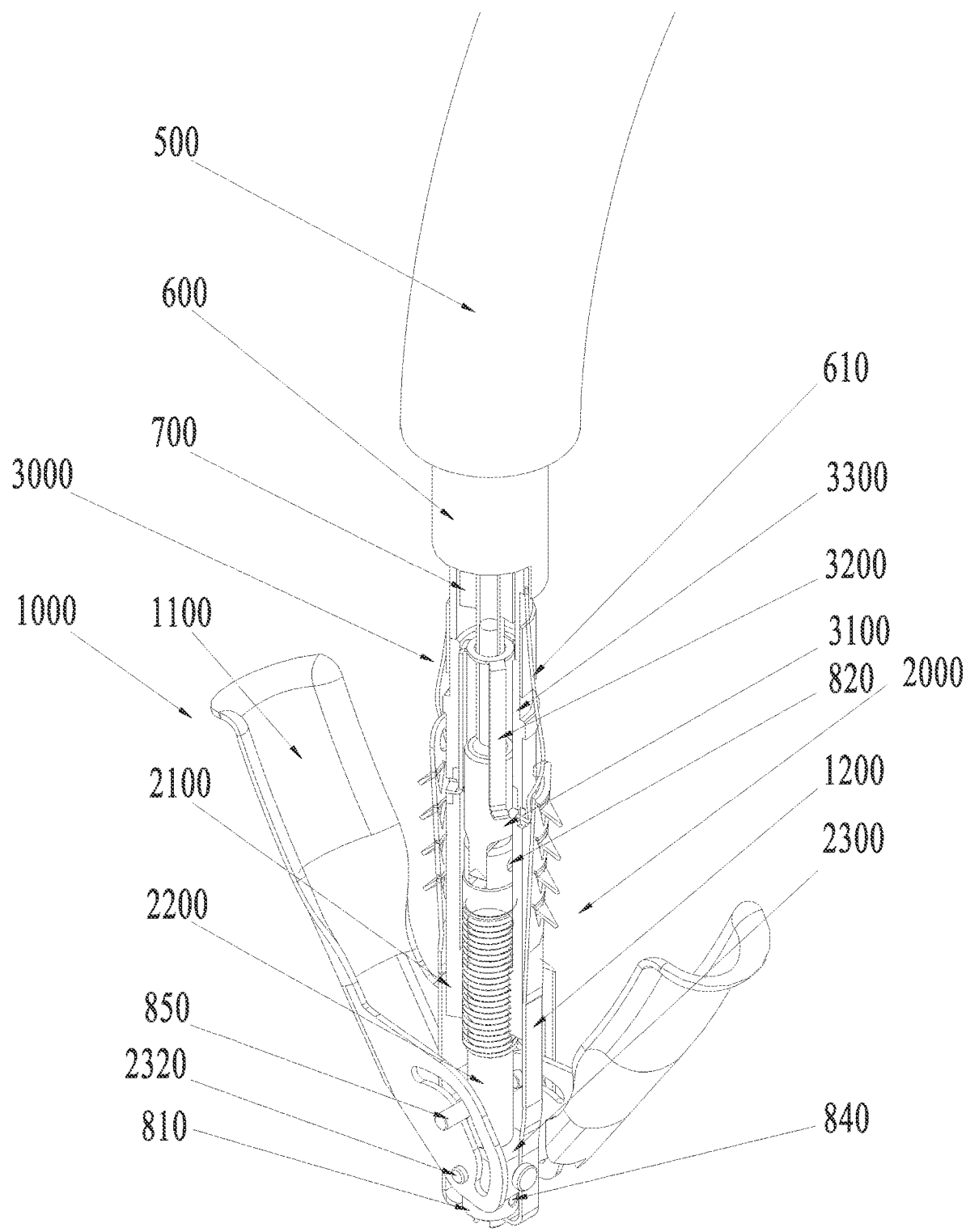
FIG. 3 is a partial sectional view of an overall structure according to the present disclosure.

Referring to FIGS. 2-4, the fixing device for clamping a tissue comprises a support mechanism 2000 comprising a fixed connecting assembly 2100 and a drive assembly 2200 that moves relative to the fixed connecting assembly; wherein the fixed connecting assembly 2100 in the support mechanism 2000 is connected to clamp mechanism 1000 at the distal end and is separably connected to the delivery control device at the proximal end through the grasping mechanism 3000.

Figure 1:
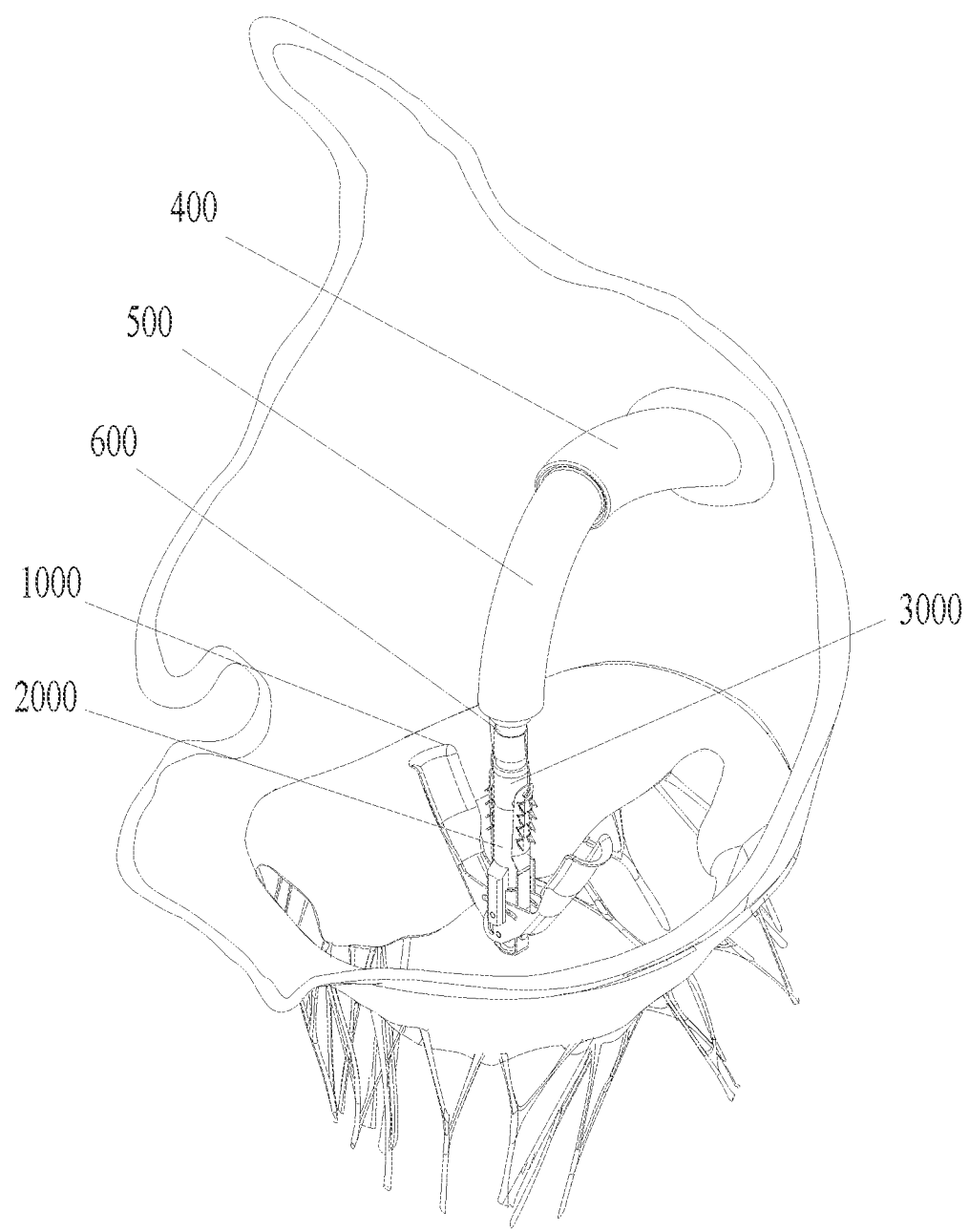
FIG. 1 shows a clamp mechanism according to one example of the present disclosure located at a mitral valve.

Specifically, the clamp mechanism 1000 in the example shown includes the pair of closure members 1100 and a pair of capture members 1200 respectively in one-to-one correspondence with the pair of closure members 1100. The closure members 1100 can be opened and closed by the drive assembly 2200. The capture members 1200 can be opened and closed by a manipulation wire 610. In order to clamp the tissue, the closure members 1100 maybe extended inward, while the capture members 1200 may be extended outward, to achieve corporation with each other. The embodiment takes clamping of a heart valve as an implementation to describe a specific working principle of the fixing device for clamping the tissue. Referring to FIG. 1, the fixing device in the example shown is delivered to a target location in a heart by the delivery control device. Specifically, the delivery control device includes a push shaft 600 for pushing or otherwise carrying the fixing device to the target location and a clutch or release mechanism 3000 for allowing the push shaft 600 and the fixing device to be separably connected. In one example, the push shaft 600 may include a rod-like body provided with an inner cavity or a hollow tubular body, which is made of a biocompatible material. In the example shown, an engagement shaft 820 is shaped as a circular rod or a circular tube. The push shaft 600 has a smooth surface to avoid damage to a valve leaflet or a chordae tendineae. The push shaft 600 first enters a surgical channel together with a catheter 500. After reaching a vicinity of the lesion, the push shaft 600 may extend out of the catheter 500 to deliver the fixing device to the mitral valve. A distal end of the fixing device, namely a distal end of the clamp mechanism 1000, is preferably coated with a protective covering layer. The protective covering layer is made of a biocompatible material and completely coats a periphery of the clamp mechanism 1000. The protective covering layer can prevent a damage of the device to the tissue. When the fixing device stays in the heart as an implant, an outer surface of the fixing device can be completely protected by the protective covering layer.

After the fixing device arrives at the valve, parts of the anterior valve leaflet and the posterior valve leaflet of the heart valve which cannot be properly closed are clamped by cooperation of the closure members 1100 and the capture members 1200 of the clamp mechanism 1000 in the embodiment. As a result, the leaflets that cannot be closed properly are clamped together, such that the mitral valve can be tightly closed or closed with a smaller opening, thereby treating or relieving "mitral regurgitation".

The clamp mechanism 1000 of other embodiments of the present disclosure can also be used to alleviate or treat "tricuspid valve regurgitation", that is, an additional one pair of the closing member 1100 and the capturing member 1200 is added on the basis of the original pair, using for the treatment of "tricuspid valve regurgitation". The principle and structure is not described in detail owing to the same as it is used for the treatment of the mitral valve regurgitation in the embodiment of the present disclosure. It can be understood that other embodiments of the present disclosure can also be applied to other minimally invasive surgeries that needs to clamp several pieces of tissue, and the number of the closure member 1100 and the capture member 1200 varies according to the actual use.

After the mitral valve is clamped, the fixing device is separated from the delivery control assembly by the grasping mechanism 3000. The fixing device remains at the lesion to fix the valve.

Regarding the clamp mechanism 1000, referring to FIG. 4, FIGS. 5A-5B, FIGS. 6A-6D, FIGS. 7A-7C, FIGS. 8A-8E, FIGS. 9A-9C and FIGS. 12A-12D, FIGS. 13A-13D again, in this embodiment, the closure member 1100 of the clamp mechanism 1000 includes a closed connecting part 1120 and a closed clamping part 1110, and the closed clamping part 1110 and the capture member 1200 are cooperated to clamp the tissue.

The guide slots 1121 are formed in the closure connecting portion 1120. A pin 850 at least partially located in the nonlinear guide slot 1121 is provided on the fixed connecting assembly 2100. The guide slot 1121 includes at least a nonlinear segment. The drive assembly 2200 is connected to the two closure clamping portions 1120, and is arranged to allow the pin 850 to slide within the guide slot 1121 when the drive assembly 2200 moves relative to the fixed connecting assembly 2100, thereby driving the two closure clamping portions 1110 to relatively move close to or away from each other.

Figure 12A:
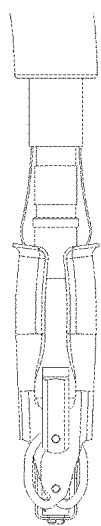
FIGS. 12A-12D each illustrate an exemplary movement process when a clamp mechanism releases a closure member according to the present disclosure.
Figure 12B:
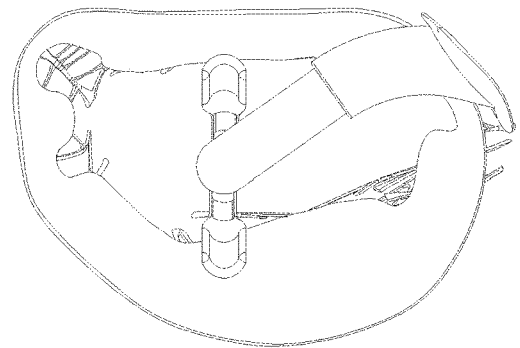
Figure 12C:
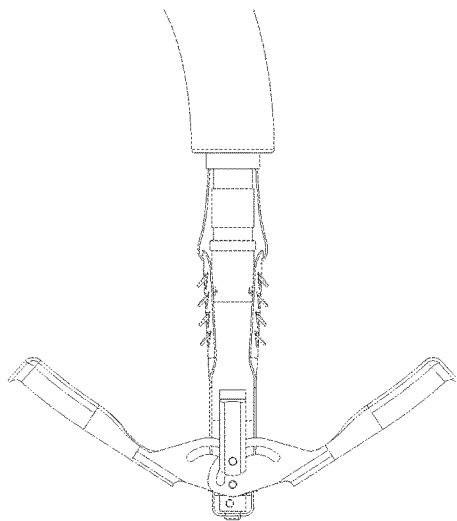
Figure 12D:
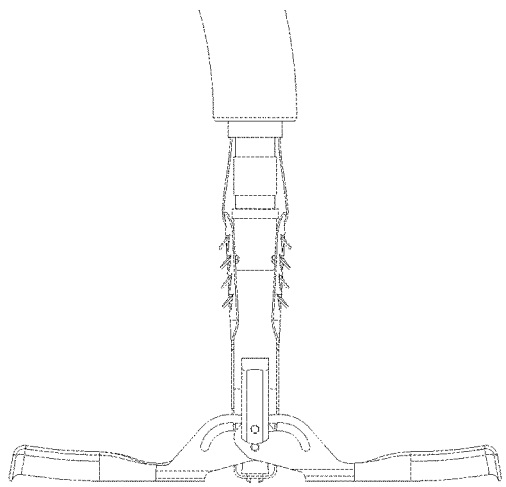

Specifically, a distal end of the closure connecting portion 1120 is rotatably connected to the drive assembly 2200, in particular to a distal end of the drive assembly 2200. In the embodiment, the closure connecting portion 1120 is provided with a connecting portion shaft hole 1122, and is connected to the drive assembly 2200 through a rotating shaft. In other embodiments, other hinged methods may be conceivable. Before the fixing device is delivered to the target location, the closure clamping portion 1110 is in an initial state in which the pin 850 is located at the proximal end of the guide chute 1121, and the closure clamping portion 1110 is closed, as shown in FIG. 12A. Under driving of the drive assembly 2200, when the rotating joint between the drive assembly 2200 and the closure connecting portion 1120 moves toward the proximal end, i.e., the connecting portion shaft hole 1122 moves toward the proximal end, the guide slot 1121 moves toward the proximal end synchronously due to the cooperation between the pin 850 and the guide slot 1121. In such a case, the pin 850, which is not moved, actually moves toward the distal end relative to the guide slot 1121. In order to make the closure clamping portion 1110 adapt to the change of distance, the pin 850 rotates the guide slot 1121 in some extent relative to the connecting portion shaft hole 1122, such that the closure clamping portion 1110 is rotated with the connecting portion shaft hole 1122 as a center. In such a case, the closure clamping portion 1110 is turned outward with the connecting portion shaft hole 1122 as an axial center, to enter the states as shown in FIGS. 12B-12C. By further driving the connecting portion shaft hole 1122 to move toward the proximal end, the closure clamping portion 1110 can enter a state, in which the two closure clamping portions 1110 form an angle of 180° relative to each other, and the distance between the end portions achieves a maximum capturing distance, as shown in FIG. 12D.

Figure 13A:
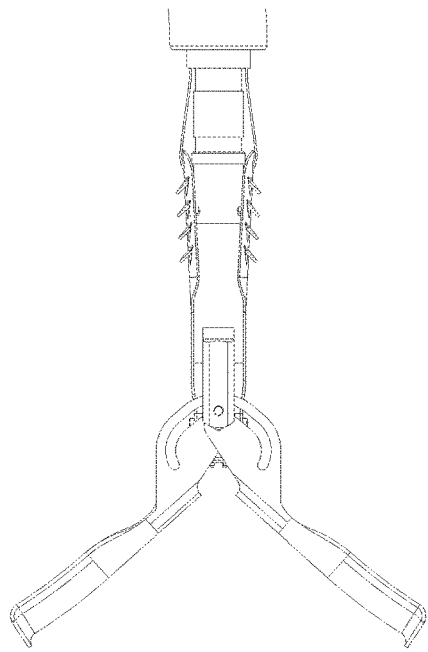
FIGS. 13A-13D each illustrate an exemplary process of capture and fixation movement of a clamp mechanism according to the present disclosure.

Benefit from the design of the guide slots 1121, the two closure clamping portions 1110 may be turned to form an angle of 180°, and further an obtuse angle as shown in FIG. 13A. It can be applied when the fixing device needs to be withdrawn from the heart in case of inaccurate location or other problems. During the moving-out process, the two closure clamping portions 1110, which form an obtuse angle, tend to incline outward relative to the contact surfaces with the tissue and would not hook the tissue. Hence, the withdrawal can be smooth and safe. The specific principle of the process in which the closure clamping portion 1110 is cooperated with the guide slot 1121 through the pin 850 to achieve the above opening angle will be described below in detail.

In the embodiment, throughout the opening and closing processes of the closure clamping portion 1110, the drive assembly 2200 moves relative to the pin 850, while the pin 850 does not move relative to the fixed connecting assembly 2100 connected therewith. Hence, during the process in which the closure clamping portion 1110 of the closure member 1100 is moved from an initial state to an open state, the closure connecting portion 1120 at the distal end moves toward the proximal end. Compared with the prior art where the clamping element is only opened and turned, the closure member 1100 in the present disclosure involves two kinds of movement in combination to allow the closure member 1100 to achieve a wider opening distance in the radial direction. Further, in the initial state of the closure clamping portion 1120, the closure connecting portion 1120 is not provided with other additional mechanisms. In such a case, a height of the overall fixing device can be lowered, and it is more convenient to turn during delivery. In view of this, the closure member 1100 can also be longer to facilitate a greater capturing distance.

After the closure clamping portion 1110 is cooperated with the capture member 1200 to clamp the tissue, the closure clamping portion 1110 further needs to be folded. When the closure clamping portion 1110 is folded, the closure connecting portion 1120 moves toward the distal end, and thus the closure clamping portion 1110 has an effect of being pulled to ward the distal end. In such a case, a characteristic of "grabbing" movement may present in the folding process. When the tissue is clamped firmly, the valve leaflet on the closure clamping portion 1110 may be "pulled" in some extent, facilitating a more firmly contact between the valve leaflet and the closure clamping portion 1110.

Figure 6A:
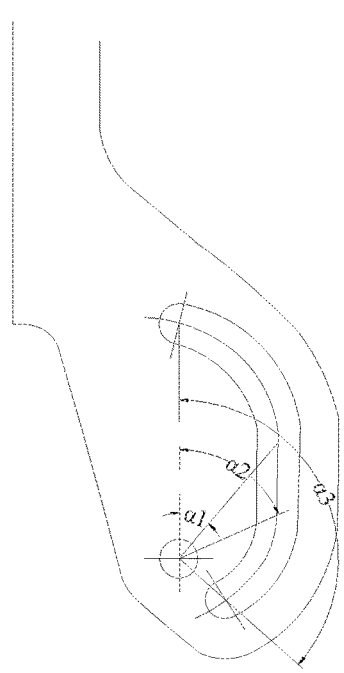
FIGS. 6A-6D each are views of an exemplary closure member according to the present disclosure.

The guide slot 1121 includes at least two guide slot regions (namely a first slot region and a second slot region) in communication with each other. A radian of the first slot region may be greater than a radian of the second slot region. FIG. 6A illustrates an implementation of the guide slot according to a first example of the present disclosure. Herein, the guide slot may be divided into a first slot region, a second slot region, and a third slot region extending from a distal end to a proximal end of each guide slot. In the example shown, the first slot region and the third slot region are arc segments defining radian $\alpha 1$ and $\alpha 3$, respectively, while the second slot region is a linear segment. With the arc feature, the turning angle can be changed in a larger range. Meanwhile, it has a small torque with a nonlinear variation in a small range, and a dead point where the torque is zero. With a linear feature, the torque is large, and changes linearly and stably. It can be changed in a larger range without a dead point, but the turning angle can be changed in a smaller range. Therefore, in the example shown in FIG. 6A, with the guide slot 1121 defined as a first curved slot region, a second linear slot region, and a third curved slot region, the closure member 1110 may experience a relatively smaller torque and a faster change process during opening at an initial position and at a position with a maximum opening angle, e.g., as the pin 850 traverses the third slot region, compared with the intermediate capturing process, and meanwhile has a relative slow angular change at the capturing process, e.g., as the pin 850 traverses the second linear slot region, thereby facilitating fine operation by the operator, and improving system reliability.

Figure 6B:
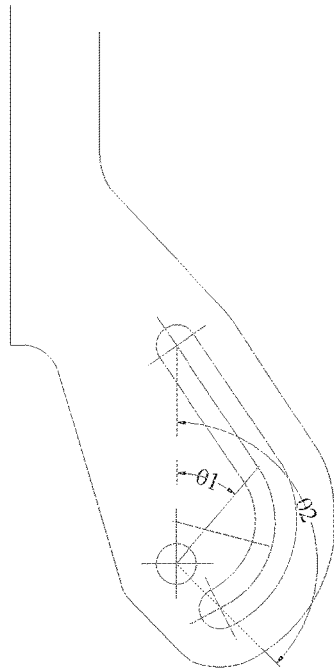
Figure 6C:
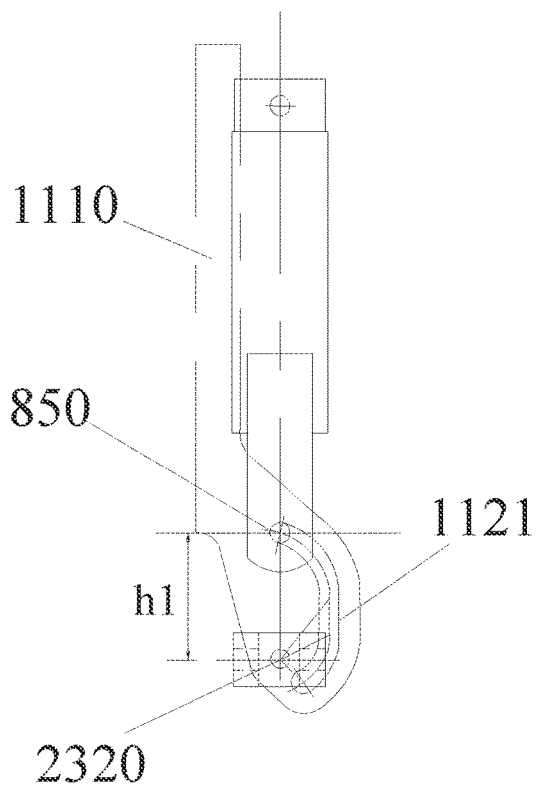
Figure 6D:
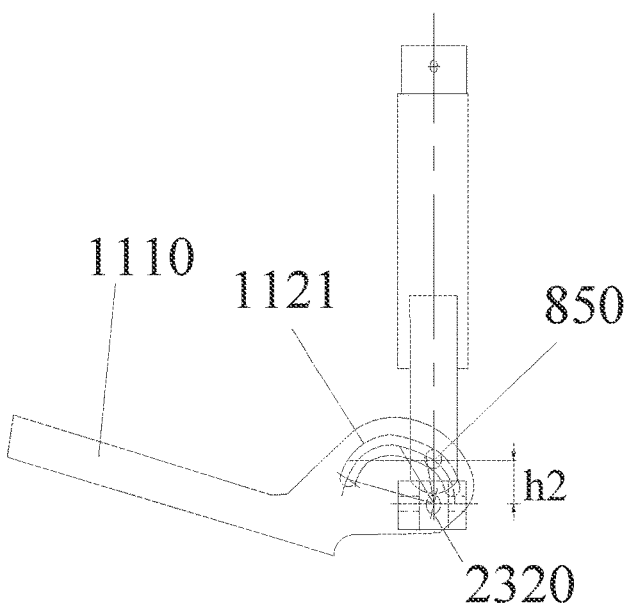

Referring to FIG. 6A and FIGS. 6C-6D, the pin 850 is shaped as a circular shaft, and located in the guide slot 1121. A width of the guide slot 1121 is matched with an outer diameter of the pin 850. At an initially unopened position, the pin 850 is located at the most proximal end, as shown in FIG. 6C, namely the most proximal end of the third slot region. A distance between the pin 850 and a closure member matching portion 2320 is h1. During opening of the closure clamping portion 1110, the pin 850 slides in the third slot region toward the distal end, and enters the second slot region from a distal-most end of the third slot region. In such a case, the closure clamping portion 1110 is rotated by an angle of $\alpha 1$. When the pin 850 further slides to a distal-most end of the second slot region, namely at an extreme end of the linear segment, the closure clamping portion 1110 is rotated by an angle of $\alpha 2$. A distance between the pin 850 and the closure member matching portion 2320 is h2, as shown in FIG. 6D. When the pin 850 further slides toward a distal end in the first slot region and arrives at a distal-most end of the guide slot 1121, the closure clamping portion 1110 is rotated by an angle of $\alpha 3$. Herein, the $\alpha 1$, the $\alpha 2$, the $\alpha 3$, the h1, and the h2 can be selected and ranged according to an actual need. In an exemplary embodiment, the angle $\alpha 1$ is preferably in a range of 30° to 45°, more preferably in a range of 35° to 40°, and even more preferably 40°. The angle $\alpha 2$ is preferably in a range of 55° to 70°, more preferably in a range of 60° to 70°, and even more preferably 65°. The angle $\alpha 3$ is preferably in a range of 120° to 150°, more preferably in a range of 125° to 135°, and even more preferably 130°. The distance h1 is preferably in a range of 15 mm to 16 mm, and more preferably 15.5 mm. The distance h2 is preferably in a range of 5 mm to 7 mm, and more preferably 6 mm. As can be seen from the above descriptions, to rotate the closure clamping portion 1110 by the angle of $\alpha 2$, the actuator needs to drive the closure member matching portion 2320 to move relative to the slot driving member 850 by a distance of h2-h1. When the angle $\alpha 2$ is 65°, h1 is 15.5 mm, and h2 is 6 mm, namely the two closure clamping portions 1110 are opened relatively at 130°, the closure member matching portion 2320 moves by a distance of 9.5 mm. With the cooperation of the first curved slot region, the second linear slot region and the third curved slot region, the closure member has the faster change process during opening at the initial position and at the position with the maximum opening angle compared with the intermediate capturing process, and meanwhile has a relative slow angular change at the capturing process, such that the capture is more stable. Compared with a common linear slot, the clamp mechanism 1000 may achieve a shorter driving distance to reach a preset capturing angle. Moreover, at a position to perform fine operation, the clamp mechanism may be safer and more reliable than that with a curved slot.

FIG. 6B illustrates another exemplary guide slot 1121 according to another embodiment of the present disclosure. In this example, the guide slot is divided into a first slot region and a second slot region from a distal end to a proximal end of the guide slot. As shown, the slot region is an arc segment, and the second slot region is a linear segment. This example is mainly intended to facilitate quick closure from the capturing position to the position with the maximum opening angle. In the tissue capturing process, the angular changing rate is reduced at the capturing segment by the linear segment, such that the capture is more stable. Specifically, from the most proximal end of the guide slot 1121 to an intersection between the first slot region and the second slot region, the pin may traverse along a varying angle of θ1, namely the pin 850 may traverse the varying angle of θ1 in the linear slot region of the guide slot 1121. With a further movement to the most distal end, the single closure clamping portion 1110 has an opening angle of θ2. Preferably, the angle θ1 is in a range of 40° to 60°, and the angle θ2 is in a range of 120° to 140°.

Referring to FIG. 3 and FIGS. 8A-8E, the drive assembly 2200 includes a movable seat 2300. The movable seat 2300 specifically includes a drive connecting member 2310. Side surfaces of the drive connecting member 2310 include first mounting surfaces and second mounting surfaces perpendicular to each other. The drive connecting member 2310 is hinged to the closure connecting portion 1120 through the closure member matching portion 2320 on the first mounting surfaces. This allows a movement of the closure member matching portion 2320, and further allows a relative movement between each guide slot 1121 and pin 850.

Figure 7A:
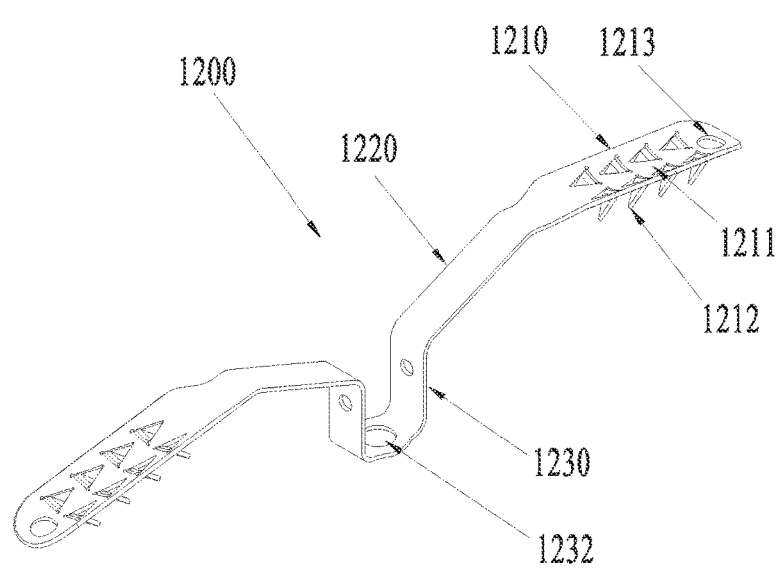
FIG. 7A is a schematic structural view of an exemplary capture member according to the present disclosure.
Figure 7B:
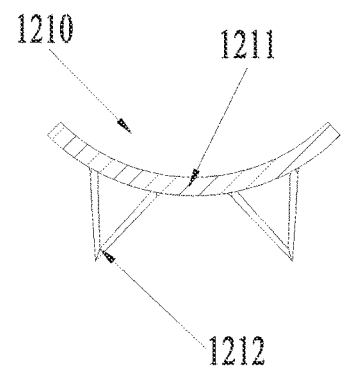
FIG. 7B is a sectional view of an exemplary capture member according to an implementation of the present disclosure.
Figure 7C:
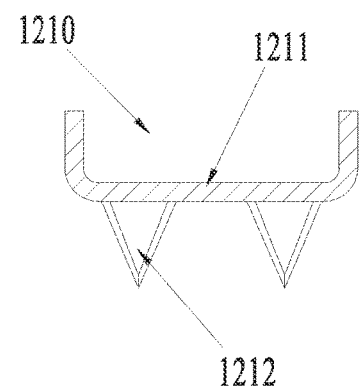
FIG. 7C is a sectional view of an exemplary capture member according to another implementation of the present disclosure.
Figure 8A:
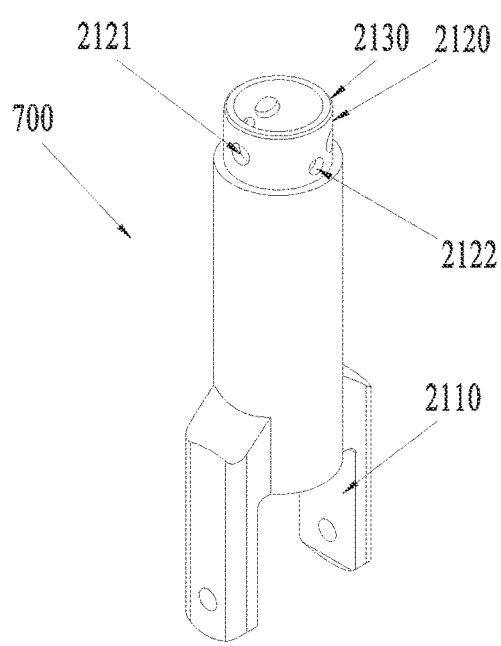
FIGS. 8A-8E each illustrate a part of an exemplary support mechanism according to the present disclosure.
Figure 8B:
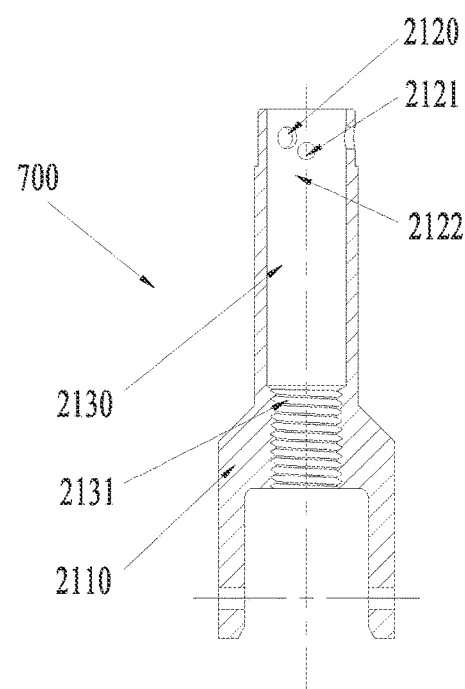
Figure 8C:
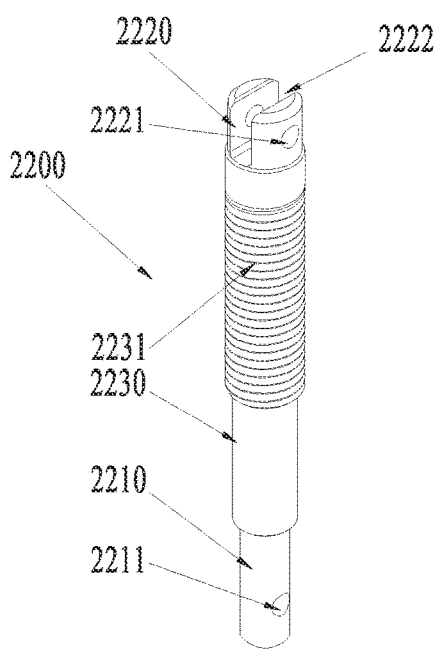
Figure 8D:
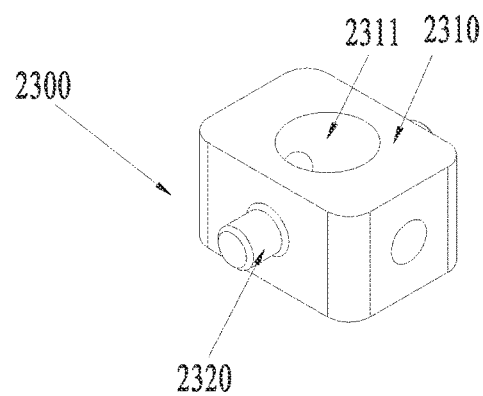
Figure 8E:
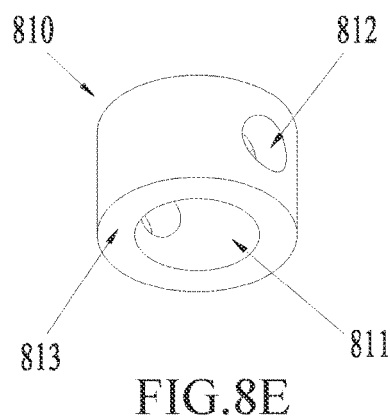
Figure 10A:
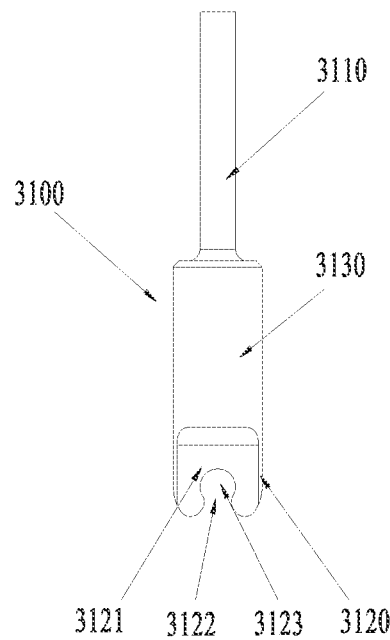
FIGS. 10A-10D each illustrate a part of an exemplary clutch mechanism according to the present disclosure.
Figure 10B:
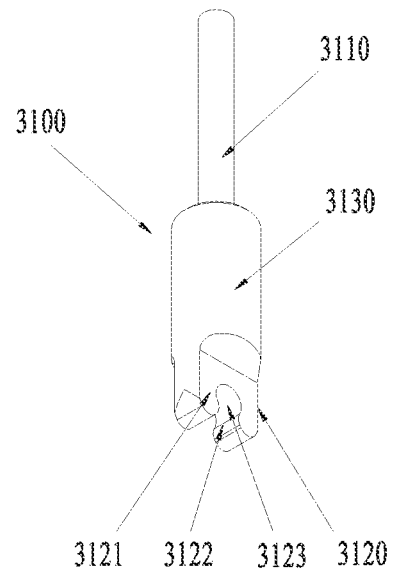
Figure 10C:
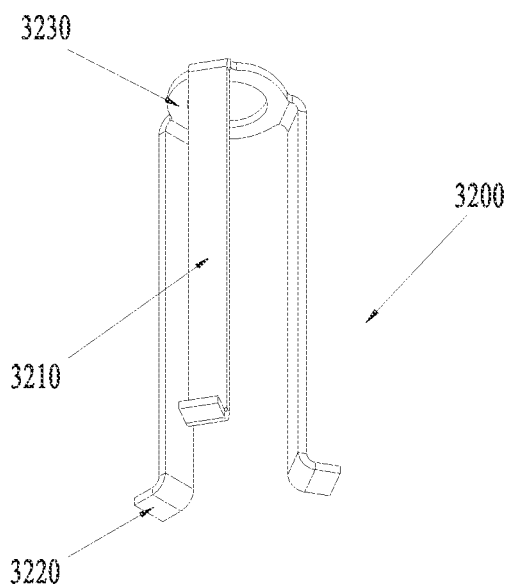
Figure 10D:
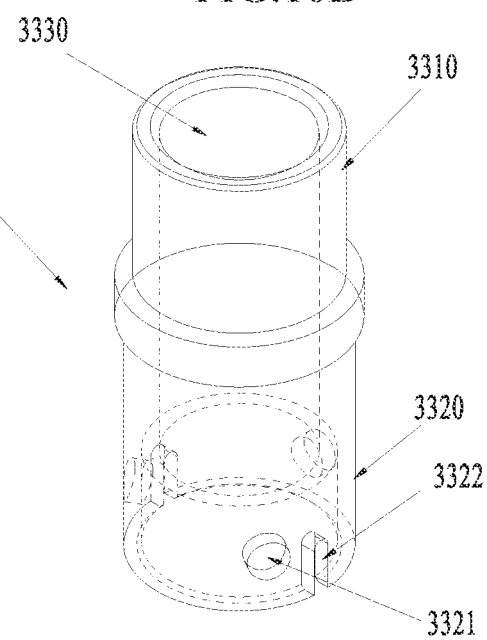

Further, referring to FIGS. 7A-7C, each one of the capture members 1200 of the clamp mechanism 1000 includes a rigid capturing portion 1210, a flexible connecting portion 1220, and a capture connecting portion 1230 that are connected sequentially. The flexible connecting portion 1220 is located between the rigid capturing portion 1210 and the capture connecting portion 1230. The second mounting surfaces are fixedly connected to the capture connecting portion 1230.

In the example shown, the capture member 1200 can cooperate with the closure member 1100 to capture a moving valve leaflet. A captured valve leaflet may be located between the closure member 1100 and the capture member 1200. The capture connecting portion 1230 may be connected to the second mounting surfaces. The capture member 1200 is shown in FIG. 7A in a relaxed or natural state, e.g., similar to spreading wings of a bird. The flexible connecting portion 1220 is specifically a deformable component with a certain resilience force. By applying an external turning force to the rigid capturing portion 1210, the flexible connecting portion 1220 elastically deforms to change an angle between the rigid capturing portion 1210 and an axial direction, thereby achieving turning of the capture member 1200. When a moving valve leaflet to be captured is located above the closure member 1100 at a same side with the capture member 1200, the elastic flexible connecting portion 1220 may be instantaneously restored to an initial shape in a natural state once the external turning force is removed. In such a case, the valve leaflet can be captured between the closure member 1100 and the rigid capturing portion 1210. In the valve capture process, the rigid capturing portion 1210 is mainly used to fix the moving valve leaflet. The structure of the rigid capturing portion 1210 needs to have a certain rigidity, so as to prevent the captured valve leaflet from escaping from the capture member 1200.

More preferably, the rigid capturing portion 1210 includes a rigid surface 1211, and capturing barbules or barbs 1212 provided outside the rigid surface. The rigid surface 1211 is uniformly thick and is bent.

The rigid surface 1211 has a rigid section, which is curved as shown in FIG. 7B or bent as shown in FIG. 7C. In the structure, the bent or curved portion is similar to a reinforcing rib formed on a main body. Consequently, the sheet-like thin-wall section has a high flexural coefficient and the rigidity of the rigid capturing portion is improved, without need of an additional component for reinforcing the rigidity. Moreover, in the example, when pushing and pulling a manipulation wire 610 (not shown, see, e.g., FIG. 11) in the delivery control assembly, the manipulation wire 610 applies a force to the capture member 1200, e.g., where q guide wire orifice 1213 is located, thereby achieving turning of the capture member 1200.

In the example, the two capture members 1200 share one capture connecting portion 1230. The capture connecting portion 1230 is U-shaped, with symmetrical vertical portions being respectively and fixedly connected to the second symmetrical mounting surfaces of the drive connecting member 2310. The capture connecting portion 1230 may be fixedly connected to the drive connecting member 2310 by hinging, riveting or welding, such that the capture member 1200 may move axially with the drive connecting member 2310. Take the pins 850 as a reference point. When the drive connecting member 2310 axially moves close to the pin 850, the closure member 1100 is opened and turned, and the overall capture member 1200 also axially moves close to the pin 850. If an external turning force toward the pin 850 is applied to the rigid capturing portion 1210 of the capture member 1200 at the same time, the capture member 1200 is turned toward the pin 850. When a suitable valve leaflet contacts the opened closure member 1100, the external turning force applied on the capture member 1200 can be removed, and the valve leaflet can be clamped between the closure member 1100 and the capture member 1200. In an embodiment, the capture member 1200 is expanded in the natural state. The manipulation wire 610 is arranged to constrict the capture member 1200 to an unexpanded state. By removing a constraint force of the manipulation wire 610, the capture member 1200 can be turned. In another embodiment, the capture member 1200 may also be a flexible member, and may be directly turned under pushing of the manipulation wire 610 for capture.

Further, when the drive connecting member 2310 starts to move axially away from the pin 850, the closure member 1100 performs closing and turning movement together with the captured valve leaflet and the opened capture member 1200. Meanwhile, the drive connecting member 2310 also moves axially away from the pin 850 together with the capture member 1200. In this case, the capture member 1200 and the valve leaflet have or trend to have a relative displacement. A pressure arising from an elastic deformation of the capture member 1200 is applied to the valve leaflet. As a consequence, a friction force occurs on a contact surface between the capture member 1200 and the valve leaflet that have the relative displacement. A direction that the capture member 1200 applies the friction force to the valve leaflet refers to a direction toward the drive connecting member 2310, such that the capture member 1200 "pulls" the valve leaflet. By increasing a friction force or features, such as the capturing barbs 1212 in the embodiment shown in FIGS. 7A-7C, on the rigid capturing portion 1210 of the capture member 1200, the valve leaflet "pulling" effect will be more evident. Compared with the proximal element that is merely turned in the background art, the clamp mechanism 1000 may provide a connection or engagement between the valve leaflet and the fixing device more firmly.

Further, referring to FIG. 3 and FIGS. 5A-5B, the closure clamping portion 1110 in the embodiment shown includes a free end and a connecting end connected to the closure connecting portion 1120. In a direction from the connecting end to the free end, an outer surface of the closure clamping portion 1110 at least partially tends to shrink toward an inner side. Due to the closure clamping portion 1110 having a concave shape with a recess, a contact area with the valve leaflet can be increased when the valve leaflet is clamped. When the closure clamping portion 1110 clamps the valve leaflet in cooperation with the capture member 1200, the valve leaflet clamped in the recess of the closure clamping portion 1110 can limit a radial displacement of the fixing device on the valve leaflet. With a flange, a damage of an edge of the closure clamping portion 1110 to the valve leaflet can be prevented. After the valve leaflet is closed by the fixing device, due to the concave bend of the closure clamping portion 1110, end portions at two sides of the closure clamping portion are formed into a receiving portion, which makes the valve leaflet to be clamped more firmly in an axial direction Further, the structure and principle of the support mechanism 2000 will be described with reference to FIG. 3 and FIGS. 8A-8E. Specifically, as mentioned above, a support mechanism 2000 comprises a fixed connecting assembly 2100 and a drive assembly 2200 that moves relative to the fixed connecting assembly 2100. The distal end of the drive assembly 2200 is connected with the closure members 1100, so that the closure member 1100 moves between open and close when the drive assembly 2200 moves relatively to the fixed connecting assembly 2100. In one embodiment, the base housing is further provided with a base lug 2110 disposed at the distal end, and the pin is disposed outside the base lug 2110. The closure member 1100 is controlled to open and close by the movement of the drive assembly 2200 relative to the pin 850.

In one embodiment, the fixed connecting assembly 2100 comprises a base housing with a base inner cavity 2130 formed therein, a base threaded portion 2131 in the base inner cavity, the drive assembly 2200 comprising a drive shaft 2230, the drive shaft 2230 comprising a drive shaft threaded portion 2231 cooperating with the base threaded portion 2131, and wherein a lead angle at which the base threaded portion 2131 is cooperating with the drive portion is less than a friction angle.

In the example, the drive shaft threaded portion 2231 and the base threaded portion 2131 slidably cooperate with each other. They have a same thread pitch and a same sectional shape. By rotating either the base housing or the shaft 2230, the base housing and the shaft 2230 can move axially relative to each other. Since a lead angle of a spiral annular groove is less than a friction angle of a contact surface between the two spiral grooves, no axial displacement would occur when the base housing or the shaft 2230 is stopped, if only an axial force is applied to the base housing or the shaft 2230. Therefore, the fixing device may provide a self-locking function without using a spring piece or other structures, unlike in the prior art, and can hold its position through a thread fit.

The drive assembly 2200 further includes a drive output shaft 2210 disposed at a distal end of the drive shaft 2230 and having an outer diameter less than that of the drive shaft 2230. The drive connecting member 2310 is provided with a connection guide hole 2311 having an inner diameter matched with the drive output shaft 2210. The drive output shaft 2210 is axially and rotatably cooperated with the connection guide hole 2311. The drive assembly 2200 further includes a locating sleeve 810 disposed at a distal end of the drive connecting member 2310. The drive output shaft 2210 extends to a locating sleeve mounting hole 811 of the locating sleeve 810 through the connection guide hole 2311, and fixedly connected to the locating sleeve 810.

As can be seen from the above structural descriptions, how the drive output shaft 2210 is movably cooperated with the drive connecting member 2310 is disclosed in the embodiment. An output end of the drive output shaft 2210 outputs thrust force and tensile force to the drive connecting member 2310, achieve axial movement of the drive connecting member 2310. However, as the drive output shaft 2210 and the base housing are rotatably moved relative to each other while the drive connecting member 2310 and the base housing are not, the above structure can realize a rotary driving process without causing any rotation movement of the clamp mechanism to rotate, and the clamp mechanism can move stably in the axial direction. The locating sleeve 810 may be a tubular part. End surfaces of the locating sleeve 810 are axial end surfaces at two sides. The locating sleeve 810 and the output end of the drive output shaft 2210 may be fixedly connected by either welding or interference fit, or mechanical connection. For example, the mechanical connection may be as follows. A locating sleeve positioning hole 812 may be formed on the locating sleeve 810 in a radial direction. A drive output shaft positioning hole 2211 is formed, in a radial direction, on the output end of the drive output shaft 2210 at the position where the output end of the drive output shaft 2210 is cooperated with the locating sleeve 810. Pins 850 are respectively provided in each of the locating sleeve positioning hole 812 and the drive output shaft positioning hole 2211.

The present disclosure also provides a system for clamping a tissue, specifically a system for clamping a heart valve in this embodiment, including the aforementioned fixing device, that is, comprising a clamp mechanism for closing a tissue, and a support mechanism carrying the clamp mechanism, the support mechanism comprising a drive assembly for driving the clamp mechanism to open and close;

a delivery control device comprising a shaft for introducing the fixing device to a target location and a grasping mechanism for enabling the shaft and the fixing device to be separably connected.

In the embodiment shown in FIG. 3, the grasping mechanism 3000 includes an elongate actuator rod or member 3100 connected to the drive assembly 2200 in a non-rotatable and axially separable manner. By rotating the actuator rod 3100, the drive assembly 2200 is driven to move axially. The actuator rod 3100 is arranged to be preset to drive the grasping mechanism 3000 to disengage from the fixing device when the actuator rod is moved proximally, e.g., after securing leaflets between the closure members 1100 and capture members 1200. Following descriptions are made to a separation principle between the grasping mechanism 3000 and the support mechanism 2000 in combination with FIG. 3, FIGS. 8A-8E and FIGS. 10A-10D.

The support mechanism 2000 for carrying the clamp mechanism 1000 includes a fixed connecting assembly 2100 and a drive assembly 2200 moveable relative to the fixed connecting assembly 2100. Specifically, the drive assembly 2200 includes an elongate shaft 2230. The shaft 2230 includes a drive shaft threaded portion 2231 in cooperation with a base threaded portion 2131. The shaft 2230 may be directed axially by rotary movement between a drive output shaft 2210 and a base housing. The drive output shaft 2210 is rotated by applying a rotating torque to the actuator rod 3100 in the grasping mechanism 3000. Specifically, the actuator rod includes an actuator rod distal or grasping end 3120 connected to the drive assembly 2200 in an axially separable and non-rotatable manner, and an actuator rod supporting portion 3130. Specifically, the drive assembly 2200 includes a transmission rod proximal or grasping end 2220. The actuator rod grasping end 3120 is non-rotatably connected to the transmission rod grasping end 2220. When a tensile force between the actuator rod grasping end 3120 and the transmission rod grasping end 2220 is greater than a preset value, the actuator rod grasping end 3120 is disengaged from the transmission rod grasping end 2220. Since a lead angle of a spiral annular groove is less than a friction angle of a contact surface between two spiral grooves, when the base housing or the drive shaft 2230 is stopped, no axial displacement will occur if an axial force is only applied to the base housing or the drive shaft 2230. Therefore, in order to disengage the actuator rod grasping end 3120 from the transmission rod grasping end 2220, the actuator rod 3100 may simply be directed proximally relative to the transmission rod grasping end 2220, thereby implementing disengagement of the fixing device from the drive assembly 2200.

Specifically, an exemplary implementation for the disengagement of the fixing device from the drive assembly 2200 is as follows.

One of the actuator rod grasping end 3120 and the transmission rod grasping end 2220 is provided with a deformable buckle 3121, while the other one of the actuator rod grasping end 3120 and the transmission rod grasping end 2220 is provided with a connecting groove 2222. The deformable buckle 3121 may be made of an elastic biocompatible material, such as a biocompatible high polymer material. The engagement shaft 820 which can be cooperatively connected to the deformable buckle 3121 is provided in the connecting groove 2222. The engagement shaft 820 is inserted into an engagement shaft hole 222. Specifically, the deformable buckle 3121 is provided with a bayonet 3122 and a clamping hole 3123 matched with the engagement shaft 820 through the bayonet 3122. The actuator rod grasping end 3120 and the transmission rod grasping end 2220 are connected to the engagement shaft 820 through the deformable buckle 3121. When the tensile force between the actuator rod grasping end 3120 and the transmission rod grasping end 2220 is greater than a preset value, the deformable buckle 3121 is disengaged from the engagement shaft 820. In the embodiment, the deformable buckle 3121 is provided at the actuator rod grasping end 3120, while the connecting groove 2222 is provided at the transmission rod grasping end 2220. However, an opposite arrangement is also conceivable.

In order to ensure an outer housing of the support mechanism 2000 is separated from an outer housing of the grasping mechanism 3000 when the actuator rod grasping end 3120 is separated from the transmission rod grasping end 2220, specifically, the grasping mechanism 3000 in the embodiment shown is further provided with a coupling seat 3300 separably connected to the base end 2120, and an engagement member 3200 for connecting the base end 2120 and the coupling seat 3300. The actuator rod 3100 is arranged to be moveable relative to the engagement member 3200 between a first position and a second position. When the actuator rod 3100 moves toward the proximal end from the second position, an actuator rod supporting portion 3130 can drive the engagement member 3200 to move toward the proximal end as well, such that the coupling seat 3300 can be relatively separated from the base end 2120. Therefore, when the actuator rod grasping end 3120 is separated from the transmission rod grasping end 2220, the coupling seat 3300 can also be synchronously separated from the base end 2120.

Specifically, the coupling seat 3300 in the embodiment shown includes a coupling seat connecting end 3310, a coupling seat distal or grasping end 3320, and a coupling seat inner cavity 3330 defined through the coupling seat 3300. The engagement member 3200 is provided in the coupling seat inner cavity 3330. The coupling seat distal end 3320 is connected to the base end 2120 via the engagement member 3200. The coupling seat connecting end 3310 is connected to a delivery device.

A main body of the base end 2120 is an extension of a tubular base structure. The coupling seat distal end 3320 can be sleeved on the base end 2120, or inserted into the base end 2120. Contact surfaces of the two ends 2120, 3320 are respectively referred to as a base matching surface and a coupling seat matching surface. A base clamping hole 2121 is formed on the base matching surface in a radial direction. Correspondingly, a coupling seat clamping hole 3321 having a same orientation is formed on the coupling seat matching surface in a radial direction. The coupling seat distal end 3320 is provided with the coupling seat clamping hole 3321. The base end 2120 is provided with the base clamping hole 2121 corresponding to the coupling seat clamping hole 3321. The engagement member 3200 includes radial tabs or other buckles 3220, each of which pass through both the coupling seat clamping hole 3321 and the base clamping hole 2121, such that the coupling seat 3300 and the base end 2120 are fixed relatively to one another. The buckle 3220 is arranged in such a manner that, when the engagement member 3200 moves toward the proximal end relative to the coupling seat 3300, the buckle 3220 gets away from the coupling seat clamping hole 3321 and/or the base clamping hole 2121, such that the coupling seat 3300 and the base clutching end 2120 can be separated from each other.

The buckle 3220 is made of a flexible material. When the engagement member 3200 moves toward the proximal end relative to the coupling seat 3300, the buckle 3220 deforms such that it can directly exit the coupling seat clamping hole 3321 and the base clamping hole 2121, without resilience to cause failure of the separation. The buckle 3220 is made of a biocompatible plastic or metal material that is not resilient after being bent.

Further, the engagement member 3200 in the embodiment shown further includes one claw bottom ring 3230 and claw connecting rods 3210. The number of the claw connecting rods 3210 is the same as the buckles 3220, and the claw connecting rods 3210 connect the buckles 3220 to the claw bottom ring 3230, respectively. The claw bottom ring 3230 is provided with a bottom ring opening. There may be three to six claw connecting rods 3210 that are uniformly connected to a side of the claw bottom ring 3230. Preferably, there are three claw connecting rods 3210. A movement of the buckle 3220 to a center is obstructed by a radial surface of the shaft-like or rod-like supporting portion 3130. It can prevent the buckle 3220 from accidentally separating from the base clamping hole 2121 and the coupling seat clamping hole 3321, and ensure the connection between the base clutching end 2120 and the coupling seat 3300.

The actuator rod 3100 further includes an actuator rod connecting end 3110 connected to a proximal end of the actuator rod supporting portion 3130. A proximal end of the actuator rod connecting end 3110 is connected to a drive source through the bottom ring opening. An outer diameter of the proximal end of the actuator rod supporting portion 3130 is greater than an inner diameter of the bottom ring opening.

The actuator rod supporting portion 3130 is shorter than each of the claw connecting rods 3210. An outer diameter of the actuator rod supporting portion 3130 is provided in such a manner that, when the actuator rod supporting portion 3130 is located in the coupling seat clamping hole 3321, an outer surface of the actuator rod supporting portion 3130 prevents the buckle 3220 from getting away from the coupling seat clamping hole 3321 and the base clamping hole 2121. Hence, the buckle 3220 deforms only when the actuator rod supporting portion 3130 contacts the claw bottom ring 3230 and further moves toward the proximal end.

On the basis of the above structure, to separate the base end 2120 from the coupling seat 3300, the actuator rod 3100 needs to move toward the claw bottom ring 3230 under an axial force. When the claw bottom ring 3230 is squeezed by the actuator rod 3100, the actuator rod supporting portion 3130 is disengaged from the buckle 3220 and no longer limits a radial movement of the buckle 3220. Under a condition of a sufficient external force, the buckle 3220 can be pulled out from the base clamping hole 2121 and the coupling seat clamping hole 3321, to achieve separation of the base end 2120 from the coupling seat 3300.

Figure 11:
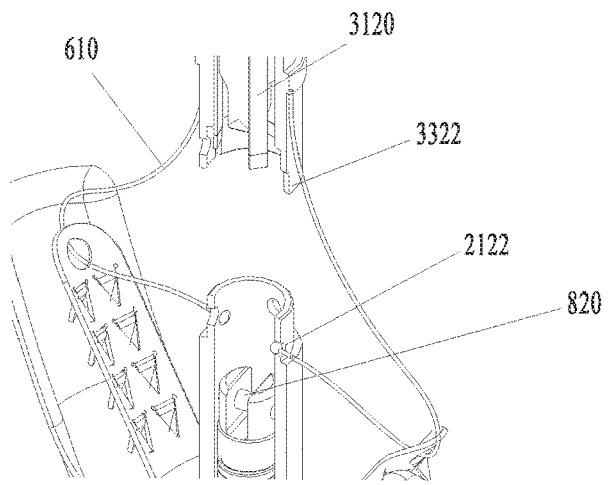
FIG. 11 is a partial enlarged view illustrating an exemplary disengagement position of a manipulation wire.

The above example is further described below. The coupling seat distal end 3320 is sleeved on the base end 2120. As shown in FIG. 11, the coupling seat 3300 includes a manipulation wire limiting groove 3322. The manipulation wire 610 for controlling the capture members 1200 of the clamp mechanism 1000 to open and close in the delivery control assembly includes an expanded head end. The expanded head end is provided in a base end hole 2122. The minimal size of the expanded head end is greater than the manipulation wire limiting groove 3322 and less than the base end hole 2122. When the coupling seat 3300 is connected the base end 2120, the separation of the manipulation wire 610 is limited through the manipulation wire limiting groove 3322.

In an embodiment, the actuator rod 3100 is provided therein with a channel extending through the proximal end to a channel of the actuator rog grasping end 3120. The actuator rod 3100 in this embodiment is internally hollow and is different from those solid ones for threaded connection in the prior art. Due to the cooperation between the connecting groove 2222 and the deformable buckle 3121, and additionally a flexible shaft for controlling a direction, an external operation structure for controlling turning can be omitted.

In order to illustrate a specific application of the device in the embodiment in surgery, an operation method of a system for clamping a tissue according to the disclosure is described in combination with specific structures in the embodiment, taking mitral valve repair as an example.

First step: pushing the fixing device with, the fixing device connected to a distal end of shaft 600, from a left atrium to a left ventricle through the mitral valve by the push shaft 600. In this case, the closure members 1100 of the clamp mechanism 1000 are in a closed state, e.g., as shown in FIG. 12A.

Second step: adjusting relative positions of the valve fixing device and the mitral valve by the shaft 600, such that the two closure members 1100 of the fixing device are respectively close to the anterior valve leaflet and the posterior valve leaflet of the mitral valve. Then, rotating the shaft 2230. The base threaded portion 2131 is cooperated with the drive shaft threaded portion 2231 to drive the drive connecting member 2310 to move toward the distal end. Taking the pin 850 as a reference point, when the drive connecting member 2310 axially moves close to the pin 850, the closure members 1100 are opened and turned to enter the states as shown in FIGS. 12B-12C. The closure members may also be further turned to enter the state as shown in FIG. 12D. In this case, the distance between the end portions of the two closure members 1100 is maximized. After the two closure clamping portions 1110 form an angle of 180°, they may further be turned to form an obtuse angle as shown in FIG. 13A, which can be applied when the fixing device needs to be withdrawn from the heart in case of inaccurate location or other problems. During the moving-out process, the two closure clamping portions 1110, which form an obtuse angle, tend to incline outward relative to the contact surfaces with the tissue and would not hook the tissue. Hence, the withdrawal can be smooth and safe.

Figure 13B:
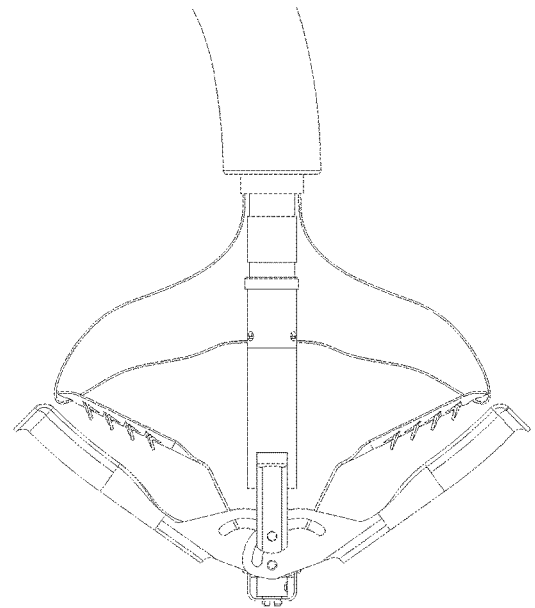

Third step: After a valve leaflet is captured by the two closure members 1100, the capture member 1200 is turned toward the closure clamping portion 1110 by the manipulation wire 610, and thus the valve leaflet can be clamped between the closure member 1100 and the capture member 1200, as shown in FIG. 13B.

Figure 13C:
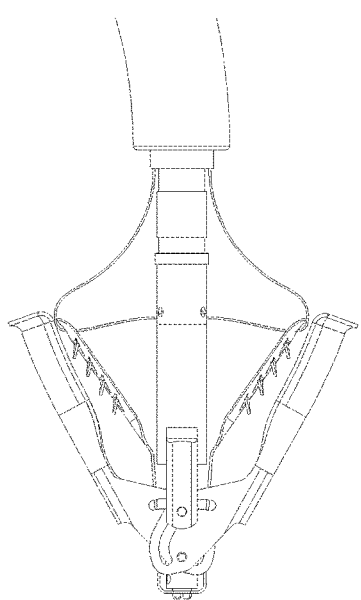
Figure 13D:
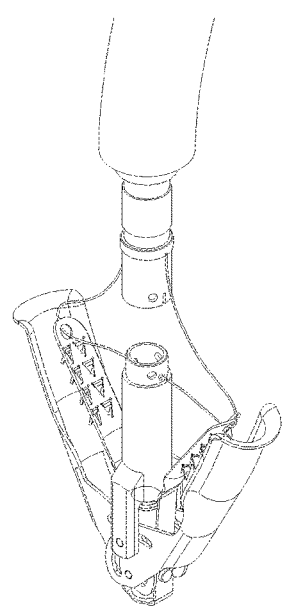

Fourth step: When the drive connecting member 2310 starts to move axially away from the pin 850, the closure member 1100 is closed and turned together with the captured valve leaflet and the opened capture member 1200. Meanwhile, the drive connecting member 2310 moves axially away from the pin 850 together with the capture member 1200 to enter the states as shown in FIGS. 13C-13D. In this case, the capture member 1200 and the valve leaflet have a relative displacement or trend to have a relative displacement. A pressure arising from an elastic deformation of the capture member 1200 is applied to the valve leaflet. As a consequence, a friction force occurs on a contact surface between the capture member 1200 and the valve leaflet that have the relative displacement. The capture member 1200 applies the friction force to the valve leaflet in a direction towards the drive connecting member 2310, such that the capture member "pulls" the valve leaflet.

When the system for clamping a tissue according to the present disclosure is applied to repair the heart valve, the closure clamping portion has an effect of being pulled to the distal end, and a "grabbing" movement may occur in the folding process. When the tissue is clamped firmly, the valve leaflet on the closure clamping portion is "pulled". By employing the guide slot having the nonlinear segment for assisting driving, and increasing the opening angle and the capturing distance of the closure member, the fixing device makes it easy to capture the valve leaflet, increase the contact with the valve leaflet, and makes the valve leaflet to be captured more firmly.

Apparently, the terms such as "front", "rear", "upper", and "lower" as used in the description, refer to position and orientation relationships of parts and components in accordance with drawings for convenience of description for the purpose of simplicity and convenience. It should be understood that such orientation terms are not intended to limit the protection scope claimed by the present disclosure.

Any one or more of the embodiments of the present disclosure and any one or more of the features in the embodiments may be combined with each other without conflict.

The above disclosed are merely preferred embodiments of the present disclosure, and are not intended to limit the claimed scope of the present disclosure. The invention is intended to cover all equivalents included within the scope of the present disclosure.

The invention claimed is:

1. A fixing device for clamping a tissue, comprising:
a support mechanism comprising a fixed connecting assembly and a drive assembly movable relative to the fixed connecting assembly; and
a clamp mechanism comprising closure members and capture portions which are in one-to-one correspondence with the closure members;
wherein each of the closure members comprises a closure connecting portion and a closure clamping portion in cooperation with respective one of the capture portions to clamp the tissue; and
wherein each of the closure connecting portions is provided with guide slots, each of the guide slots comprises, from a distal end to a proximal end thereof, at least a first slot portion and a second slot portion which is in communication with the first slot portion and has a radian smaller than that of the first slot portion, the fixed connecting assembly is provided with two pins at least partially located in the guide slots, respectively, and the fixed connecting assembly and the two closure connecting portions are arranged in such a manner that the two pins are slidable relative to the guide slots when the drive assembly moves relative to the fixed connecting assembly, so as to drive the two closure clamping portions of the clamp mechanism to move towards or away from each other.

2. The fixing device according to claim 1, wherein each of the pins are located at or near a proximal end of respective one of the guide slots when the closure clamping portions are closed.

3. The fixing device according to claim 1, wherein the first slot portions are arc segments, and the second slot portions are linear segments.

4. The fixing device according to claim 1, wherein each of the guide slots further comprises a third slot portion in communication with the respective second slot portion and having a radian greater than the radian of the respective second slot portion, and the second slot portions are located between the first slot portions and the third slot portions, respectively.

5. The fixing device according to claim 4, wherein the first slot portions and the third slot portions are arc segments, and the second slot portions are linear segments.

6. The fixing device according to claim 1, wherein the drive assembly comprises a drive connecting member, and side surfaces of the drive connecting member include first mounting surfaces and second mounting surfaces perpendicular to the first mounting surfaces;
the drive connecting member is hinged to the closure connecting portion through a closure member matching portion on the first mounting surfaces.

7. The fixing device according to claim 1, wherein each one of the capture portions includes a rigid capture portion, a capture connecting portion and a flexible connecting portion located between the rigid capture portion and the capture connecting portion, and the second mounting surfaces are fixedly connected to respective one of the capture connecting portions.

8. The fixing device according to claim 4, wherein, when the closure clamping portions are in an unopen position, each of the pins is located at or near a most proximal end of corresponding one of the third slot portions.

9. The fixing device according to claim 8, wherein, when the closure clamping portions are rotated from the unopen position by a first angle, each of the pins is located at a joint of respective one of the second slot portions and respective one of the third slot portions.

10. The fixing device according to claim 8, wherein, when the closure clamping portions are rotated from the unopen position by a second angle, each of the pins is located at a joint of respective one of the second slot portions and respective one of the first slot portions.

11. The fixing device according to claim 8, wherein, when the closure clamping portions are rotated from the unopen position by a third angle, each of the pins is located at or near a most distal end of respective one of the first guide slots.

12. A system for clamping a tissue, comprising
the fixing device according to claim 1;
a delivery control device comprising a shaft for introducing the fixing device to a target location and a grasping mechanism for enabling the shaft and the fixing device to be separably connected.

13. A method for clamping tissues by using the fixing device according to claim 1, comprising:
delivering the fixing device to a target location;
adjusting the closure members of the fixing device to approach/contact the tissues
controlling the capture portions of the fixing device so as to clamp the tissues between the closure members and the capture portions; and
adjusting the closure members to a right position before the fixing device self-locks.

14. The method according to claim 13, wherein the closure members of the fixing device are in a closed state in the step of delivering the fixing device to a target location.

15. The method according to claim 13, wherein the step of adjusting the closure members of the fixing device to approach/contact the tissues comprises pivoting the closure members of the fixing device to locate the tissues between the closure members and the capture portions of the fixing device.

16. The method according to claim 15, wherein, during the step of pivoting the closure members of the fixing device to locate the tissues between the closure members and the capture portions of the fixing device, the pins are displaced relative to the guide slots such that the two closure clamping portions move away from each other.

* * * * *